United States Patent [19]

Rasberger et al.

[11] 4,238,613

[45] Dec. 9, 1980

[54] POLYALKYLPIPERIDINE DERIVATIVES

[75] Inventors: Michael Rasberger, Riehen; Friedrich Karrer, Zofingen, both of Switzerland

[73] Assignee: Ciba-Geigy Corporation, Ardsley, N.Y.

[21] Appl. No.: 951,218

[22] Filed: Oct. 13, 1978

Related U.S. Application Data

[63] Continuation of Ser. No. 861,052, Dec. 15, 1977, abandoned.

[30] Foreign Application Priority Data

Dec. 23, 1976 [CH] Switzerland ............... 016262/76

[51] Int. Cl.$^3$ ................ C07D 211/08; C07D 211/60; C07D 211/32; C07D 211/20
[52] U.S. Cl. ................................ 546/190; 546/191; 546/230; 546/235; 546/236; 546/237

[58] Field of Search ............... 546/191, 190, 230, 235, 546/236, 237

[56] References Cited

U.S. PATENT DOCUMENTS

2,980,673   4/1961   Hidalgo ........................... 546/190

Primary Examiner—Henry R. Jiles
Assistant Examiner—Robert C. Whittenbaugh
Attorney, Agent, or Firm—Harry Falber

[57] ABSTRACT

Polyalkylpiperidinylesters and N-polyalkylpiperidinylamides of substituted malonic acids, methane tricarboxylic acids, β-keto-, α-cyano-, α-phosphono- or α-sulfonocarboxylic acids are excellent stabilizers for polymers, especially against photochemical degradation. Polymers which can be stabilized in this way very effectively are polyolefins, styrene homo- and copolymers, polyamides and polyurethanes.

7 Claims, No Drawings

POLYALKYLPIPERIDINE DERIVATIVES

This is a continuation of application Ser. No. 861,052, filed on Dec. 15, 1977, now abandoned.

The invention relates to new polyalkylpiperidine derivatives of mono- and preferably poly-carboxylic acids, their manufacture and their use as stabilisers for plastics and to the material stabilised with these derivatives.

The derivatives concerned are compounds of the formula I or II

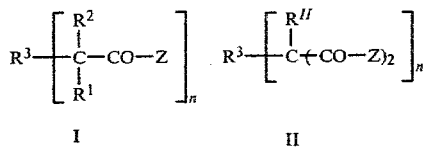

and their salts, in which n is 1 or 2, Z is a group of the formula III, IV or V

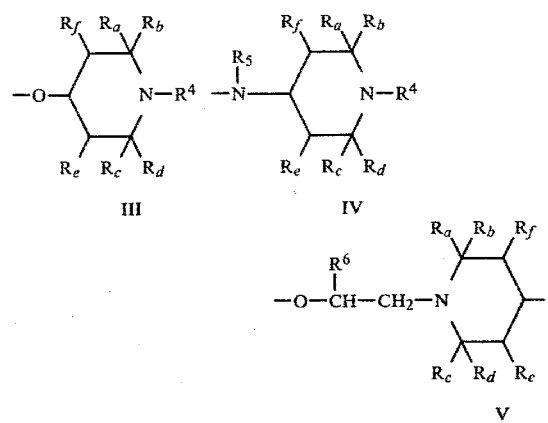

in which $R^4$ represents hydrogen, O; —OH, alkyl with 1–12 C atoms, alkenyl with 3 or 4 atoms, propargyl, benzyl or a group of the formula —CH$_2$—CH(OR$^9$-)—F$^8$, in which $R^8$ denotes hydrogen, methyl or phenyl and $R^9$ denotes hydrogen or a group A—CO—; or $R^4$ denotes a group A—CO— and in both cases A denotes alkyl with 1–17 C atoms, alkenyl with 2 or 3 C atoms, cyclohexyl, phenyl, benzyl or a phenyl, phenylmethyl or phenylethyl group which is substituted by 2 alkyl groups, each with 1–4 C atoms, and a hydroxyl group, or denotes alkylamino with 1–12 C atoms, dialkylamino with 2–16 C atoms, anilino, alkoxy with 1–12 C atoms, benzyloxy or phenoxy, $R^5$ denotes hydrogen, alkyl with 1–18 C atoms, alkenyl with 3–6 C atoms, propargyl, cycloalkyl with 5–12 C atoms, aralkyl with 7–14 C atoms, which can be substituted by OH, or a group of the formula VI

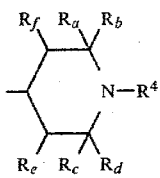

$R^6$ is hydrogen, methyl or phenyl, $R^7$ denotes hydrogen, —OR$^{10}$ or —N(R$^{11}$)(R$^{12}$) and $R^{10}$ denotes alkyl with 1–18 C atoms, alkenyl with 3–6 C atoms, benzyl, 2-cyanoethyl or an aliphatic, cycloaliphatic, aromatic or araliphatic acyl group which has up to 18 C atoms and can be substituted in the aromatic part by halogen, alkoxy with 1–4 C atoms, alkyl with 1–4 C atoms and/or hydroxyl, $R^{11}$ is alkyl with 1–18 C atoms, alkenyl with 3–6 C atoms or phenylalkyl with 7–9 C atoms and $R^{12}$ has the same meaning as $R^{11}$ or represents an aliphatic, cycloaliphatic, aromatic or araliphatic acyl group which has up to 18 C atoms and can be substituted in the aromatic part by halogen, alkoxy with 1–4 C atoms, alkyl with 1–4 C atoms and/or hydroxyl, $R_a$ denotes alkyl with 1–6 C atoms, $R_b$ denotes alkyl with 1–6 C atoms, $R_c$ denotes alkyl with 1–9 C atoms, phenyl, benzyl or phenylethyl and $R_d$ denotes alkyl with 1–6 C atoms, or $R_c$ and $R_d$ conjointly denote tetramethylene or pentamethylene, $R_e$ denotes hydrogen, alkyl with 1–5 atoms, alkenyl or alkinyl with 3–4 C atoms or benzyl and $R_f$ denotes hydrogen, alkyl with 1–5 C atoms or benzyl and the positions of $R_e$ and $R_f$ can be exchanged, and $R^1$ denotes one of the groups —CN, —CHO, —COR$^{13}$, —SO$_2$R$^{13}$, —P(O)(OR$^{14}$)$_2$, —P(O)(C$_6$H$_5$)$_2$, —COOR$^{15}$ or —CON(R$^{16}$)(R$^{17}$), in which $R^{13}$ denotes alkyl with 1–18 C atoms, cyclohexyl, aryl which has 6–10 C atoms and can be substituted by chlorine or C$_1$–C$_8$-alkyl, phenylalkyl with 7–9 C atoms or a phenyl or phenylalkyl radical which is substituted by one or two C$_1$–C$_4$-alkyl groups and/or hydroxyl, $R^{14}$ denotes alkyl with 1–18 C atoms, aryl with 6–10 C atoms or aralkyl with 7–9 C atoms, $R^{15}$ denotes alkyl with 1–18 C atoms, alkenyl with 3–6 C atoms, phenyl, phenylalkyl with 7–9 C atoms or alkylphenyl with 7–14 C atoms and $R^{16}$ and $R^{17}$ independently of one another denote hydrogen, alkyl with 1–12 C atoms, cyclohexyl, benzyl or phenyl, $R^2$ denotes hydrogen, alkyl with 1–20 C atoms, alkenyl or alkinyl with 3–4 C atoms, aralkyl with 7–14 C atoms, phenyl, —COZ, —COOR$^{15}$ or an alkyl group which has 1–10 C atoms and is substituted by one or two of the groups —CN, —COZ, —P(O)(OR$^{14}$)$_2$, —COOR$^{15}$ or —CON(R$^{16}$)(R$^{17}$) on different C atoms, or denotes a group of the formula VI, and, when n is 1, $R^{II}$ denotes —COZ, —COOR$^{15}$ or an alkyl group which has 1–10 C atoms and is substituted by one or two of the groups —CN, —COZ, —P(O)(OR$^{14}$)$_2$, —COOR$^{15}$ or —CON(R$^{16}$)(R$^{17}$) on different C atoms, or denotes a group of the formula VI, and, if $R^3$ is a —COZ group, can also be hydrogen, and when n is 2, $R^{II}$ can also denote alkyl with 1–20 C atoms, alkenyl or alkinyl with 3–4 C atoms, aralkyl with 7–11 C atoms or phenyl, and when n is 1, $R^3$ denotes alkyl with 1–20 C atoms or an alkyl group which has 1–10 C atoms and is substituted by one or more of the groups —CN, —COZ, —COOR$^{15}$, —SO$_2$R$^{13}$, —CON(R$^{16}$)(R$^{17}$), —COR$^{18}$ or —P(O)(OR$^{14}$)$_2$, in which $R^{18}$ denotes alkyl with 1–12 C atoms, or $R^3$ denotes a group of the formula

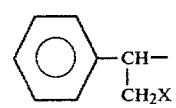

in which X represents —CN, —COR$^{19}$, —COOH, —COOR$^{20}$ or —COZ, $R^{19}$ represents alkyl with 1–5 C atoms or phenyl and $R^{20}$ represents alkyl with 1–18 C atoms, allyl, cyclohexyl or benzyl, and $R^3$ furthermore represents one of the groups —COZ or —COOR$^{15}$, an alkyl group which has 3–18 C atoms and is interrupted by —SO$_2$—, or alkenyl with 3–18 C atoms, alkinyl with 3–8 C atoms, cycloalkyl with 5–12 C atoms, alkylcycloalkyl with 6–18 C atoms, cycloalkyl-alkyl with 6–14 C atoms, aralkyl or alkyl-aralkyl with 7–19 C atoms, phenyl or a group —OR$^{21}$, in which R$^{21}$ can be alkyl with 1–18 C atoms, alkenyl with 3–4 C atoms, alkinyl with 3–4 C atoms or phenylalkyl with 7–9 C atoms, or R$^3$ represents a group —O—C(O)R$^{22}$ or —NH—C-(O)R$^{22}$, in which R$^{22}$ can be alkyl with 1–12 C atoms, alkenyl with 2 or 3 C atoms, cyclohexyl, phenyl, benzyl or a phenyl, phenylmethyl or phenylethyl group which is substituted by 2 alkyl groups, each with 1–4 C atoms, and a hydroxyl group, or R$^3$ represents a group of the formula VII

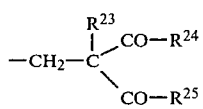

in which R$^{23}$ represents alkyl with 1–20 C atoms, allyl, benzyl, phenyl or a group —O—C(O)R$^{22}$ or —NH—C-(O)R$^{22}$, which is as defined above, and R$^{24}$ and R$^{25}$ independently of one another represent alkoxy with 1–6 C atoms or have one of the meanings indicated for Z and, when n is 2, R$^3$ represents a direct bond, alkylene with 1–20 C atoms, alkylene which has 2–10 C atoms and is interrupted by —O—, arylene-bis-alkylene with 8–14 C atoms, alkenylene with 4–8 C atoms, alkinylene with 4–8 C atoms or a group of the formula —C$_m$H$_{2m}$—COO—Y—OCO—C$_m$H$_{2m}$—, in which Y denotes alkylene with 2–12 C atoms, butenylene, butinylene, cyclohexylene or a group of the formula VIII

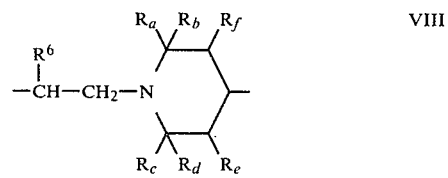

and m denotes a number from 1 to 4, but R$^1$ cannot be the group —CN when one of the substituents R$^2$, R$^{II}$ or R$^3$ has the meaning —COZ.

In the meaning of alkyl with 1–5 C atoms, R$_e$ and R$^{19}$ can be, for example, methyl, ethyl, propyl, sec.-butyl or amyl. As alkyl, R$^4$, R$^{16}$, R$^{17}$ and R$^{22}$ can, moreover, also be, for example, hexyl, octyl, 2-ethylhexyl, iso-nonyl, decyl or dodecyl. As alkyl, R$^5$, R$^{10}$, R$^{11}$, R$^{12}$, R$^{13}$, R$^{14}$, R$^{15}$, R$^{18}$, R$^{20}$ and R$^{21}$ can, moreover, also be, for example, tridecyl, hexadecyl or octadecyl. As alkyl, R$^3$ and R$^{23}$ can, moreover, also be nonadecyl or eicosyl.

In the meaning of alkyl interrupted by SO$_2$, R$^3$ can be, for example, 2-(methylsulphonyl)-ethyl, 2-(tert.-butylsulphonyl)ethyl, 3-(dodecylsulphonyl)-propyl or 2-(dodecylsulphonyl)propyl.

In the meaning of alkenyl with 2–3 C atoms, R$^{22}$ can be vinyl or propenyl. As alkyl with 3–4 C atoms, R$^2$, R$^4$, R$^7$, R$^{11}$, R$^{12}$ and R$_e$ can be, for example, allyl or methallyl. As alkenyl with 3–6 C atoms, R$^{15}$ can, moreover, also denote pentenyl or hexenyl. As alkenyl, R$^3$ can also be, for example, octenyl, undecenyl or oleyl.

As alkinyl with 3–4 C atoms, R$^2$, R$^{21}$ and R$^{21}$ and R$_e$ can be, for example, propargyl or 2-butinyl-1. As alkinyl, R$^5$ can, moreover, also be pentinyl or hexinyl and, as alkinyl, R$^3$ can, in addition, also denote heptinyl or octinyl.

In the meaning of cycloalkyl with 5–8 C atoms, R$^5$ can be, for example, cyclopentyl, cyclohexyl or cyclooctyl. As cycloalkyl, R$^3$ and R$^{12}$ can, moreover, also be, for example, cyclodecyl or cyclododecyl. R$^3$ can also be alkylcycloalkyl with 6–18 C atoms, such as, for example, methylcyclohexyl or diethylcyclooctyl, or also cycloalkylalkyl with 6–14 C atoms, such as, for example, cyclohexylmethyl, cyclohexylethyl or cyclododecylmethyl.

As phenylalkyl with 7–9 atoms, R$^{12}$, R$^{13}$, R$^{14}$, R$^{15}$ and R$^{21}$ can be, for example, benzyl, phenylethyl or phenylpropyl. In the meaning of aralkyl with 7–11 C atoms, R$^2$ can be, for example, benzyl, phenylethyl, phenylpropyl or naphthylmethyl. As aralkyl with 7–14 C atoms, R$^5$ can, moreover, also be, for example, diphenylylmethyl, naphthylpropyl or diphenylmethyl. As alkylaralkyl with 7–19 C atoms, R$^3$ can be, for example, 4-methylbenzyl, 4-tert.-butylbenzyl, 2,4-dimethylbenzyl or 4-nonylbenzyl.

In the meaning of aryl with 6–10 C atoms, R$^{14}$ can be phenyl or naphthyl and, as aryl, R$^{13}$ can, moreover, also be, for example, 4-chlorophenyl, 5-chloro-1-naphthyl, p-tolyl, 4-tert.-butylphenyl or 4-isopropyl-1-naphthyl. As alkylphenyl with 7–14 C atoms, R$^{15}$ can be, for example, tolyl, isopropylphenyl or p-tert.-octylphenyl.

As alkoxy with 1–6 C atoms, R$^{24}$ and R$^{25}$ can be, for example, methoxy, ethoxy, butoxy or hexoxy.

If R$^4$ and/or R$^9$ represent a group A—CO—, this can be, depending on the meaning of A, a carboxylic acid radical, such as, for example, acetyl, propionyl, butyryl, capronyl, capryloyl, lauroyl, acryloyl, crotonoyl, phenylacetyl- or β-(3,5-di-tert.-butyl-4-hydroxyphenyl)-propionyl and -acetyl or benzoyl; or a carbamoyl radical, such as, for example, methylcarbamoyl, butylcarbamoyl, dodecylcarbamoyl, diethylcarbamoyl, dihexylcarbamoyl, dioctylcarbamoyl or phenylcarbamoyl; or a carboxylic acid ester radical, such as, for example, ethoxycarbonyl, isopropoxycarbonyl, 2-ethylhexyloxycarbonyl, dodecyloxycarbonyl, benzyloxycarbonyl or phenoxycarbonyl.

If R$^{10}$ and/or R$^{12}$ represent an aliphatic, cycloaliphatic, aromatic or araliphatic acyl group which has up to 18 C atoms and can be substituted in the aromatic radical by halogen, alkoxy, alkyl or OH, this group can be, for example, acetyl, propionyl, isobutyryl, capronyl, capryloyl, lauroyl, stearoyl, oleyl, cyclohexanecarbonyl, benzoyl, 4-chlorobenzoyl, toluoyl, 3-methoxybenzoyl, 2,4-dichlorobenzoyl, 4-tert.-butylbenzoyl, phenylacetyl, 3,5-di-tert.-butyl-4-hydroxybenzoyl or 4-chlorophenylpropionyl.

As an alkylene radical with 1–20 C atoms, R$^3$ can be a straight-chain or branched alkylene radical, such as, for example, methylene, 1,2-ethylene, trimethylene, 1,2-propylene, tetramethylene, 2,2-dimethyl-1,3-propylene, hexamethylene, octamethylene, dodecamethylene or eicosamethylene. As alkylene with 2–12 C atoms, Y can be, for example, 1,2-ethylene, 1,2-propylene, 1,4-butylene or decamethylene.

As alkenylene or alkinylene with 4–8 C atoms, R$^3$ can be, for example, 2-butenylene-1,4, 2-butinylene-1,4, 3-hexenylene-1,6, 2-ethyl-2-butinylene-1,4 or 2,3-diethyl-2-butinylene-1,4.

If R$^3$ represents an alkylene group interrupted by —O—, this group can be, for example, 3-oxa-1,5-pentylene or 4-oxa-1,7-heptylene. As arylene-bis-alkylene with 8–14 C atoms, $R^3$ can be, for example, p- or m-xylylene or diphenyl-1,4-dimethylene.

The compounds of the formulae I and II provide plastics with outstanding protection against thermo-oxidative degradation, but above all against photochemical degradation. It is known from recent publications that derivatives of polyalkylpiperidines are good light stabilisers for plastics and, above all, carboxylic acid esters of 4-hydroxy-polyalkylpiperidines, such as are described in German Offenlegungsschriften Nos. 1,929,928, 2,204,659, 2,258,752 and 2,623,422, and carboxylic acid amides of 4-amino-polyalkylpiperidines, such as are described in German Offenlegungsschriften Nos. 2,040,975, 2,349,962 and 2,621,870, are distinguished by their high effectiveness. In the case of plastics which are processed at relatively high temperatures (above 200° C.), the volatility of these piperidinol esters becomes apparent as a disadvantage. In the case of polymers which are frequently in contact with water when they are used, the inadequate stability of such piperidine derivatives, for example the amides, to extraction also becomes apparent as a disadvantage. The piperidinol esters can be hydrolysed when subjected to the prolonged action of water. Thus, despite the outstanding light stabilising action of the known ester and amide derivatives of polyalkylpiperidines, there is a need for derivatives of this type which do not display the disadvantages mentioned, or display these disadvantages to a lesser extent. It has been found that the compounds of the formulae I and II, defined above, possess, coupled with an outstanding light stabilising action for a large number of plastics, a greater thermal stability, better stability to extraction and/or better stability to hydrolysis than the known piperidine stabilisers.

Amongst the compounds of the formulae I and II, those in which Z is one of the groups of the formulae III, IV or V, in which $R^4$ represents hydrogen, O; alkyl with 1–8 C atoms, allyl, propargyl, benzyl, formyl, acetyl, acryloyl or crotonoyl, $R^5$ represents hydrogen, alkyl with 1–12 C atoms, cyclohexyl, benzyl or phenyl, $R^6$ represents hydrogen, $R^7$ represents hydrogen or —$OR^{10}$ and $R^{10}$ represents hydrogen, alkyl with 1–6 C atoms, alkanoyl with 2–12 C atoms, benzoyl or benzyl, $R_a$, $R_b$, $R_c$ and $R_d$ are methyl and $R_e$ and $R_f$ are hydrogen, or $R_a$ and $R_c$ are ethyl, $R_b$, $R_d$ and $R_e$ are methyl and $R_f$ is hydrogen, are preferred.

Furthermore, those compounds of the formulae I and II in which $R^1$ denotes —CN, —CHO, —$COR^{13}$, —P(O)($OR^{14}$)$_2$ or —$COOR^{15}$, in which $R^{13}$ represents alkyl with 1–4 C atoms or phenyl, $R^{14}$ represents alkyl with 1–4 C atoms and $R^{15}$ represents alkyl with 1–12 C atoms, $R^2$ denotes alkyl with 1–20 C atoms, hydrogen, allyl, propargyl, benzyl, —COZ, —$COOR^{15}$, a group of the formula VI or a $C_1$–$C_4$-alkyl which is substituted by 1 or 2 of the groups —CN, —COZ, —P(O)($OR^{14}$)$_2$, —$COOR^{15}$ or —CON($R^{16}$)($R^{17}$) on different C atoms, and $R^{16}$ and $R^{17}$ independently of one another are hydrogen, $C_1$–$C_{12}$-alkyl, cyclohexyl or benzyl, and when n is 1, $R^{II}$ denotes —COZ, —$COOR^{15}$, a group of the formula VI or a $C_1$–$C_4$-alkyl which is substituted by 1 or 2 of the groups —CN, —COZ, —P(O)($OR^{14}$)$_2$, —$COOR^{15}$ or —CON($R^{16}$)($R^{17}$) on different C atoms and, when n is 2, $R^{II}$ can also denote alkyl with 1–20 C atoms, allyl, propargyl or benzyl, and, if n is 1, $R^3$ denotes alkyl with 1–12 C atoms, a $C_1$–$C_4$-alkyl group substituted by one of the groups —CN, —$COR^{13}$ or —P(O)($OR^{14}$)$_2$ or by one or two of the groups —COZ, —$COOR^{15}$ or CON($R^{16}$)($R^{17}$), or denotes a group of the formula VII, in which $R^{21}$ is $C_1$–$C_{12}$-alkyl or benzyl and $R^{22}$ and $R^{23}$ represent $C_1$–$C_6$-alkoxy or have the meaning indicated for Z, or, if n is 2, $R^3$ represents alkylene with 1–12 C atoms, arylene-bis-alkylene with 8–14 C atom butenylene, butinylene or a group of the formula —$C_mH_2M$—COO—Y—OCO—$C_mH_{2m}$—, in which Y denotes $C_2$–$C_8$-alkylene and m denotes 1 or 2, are preferred.

Those compounds of the formulae I and II in which Z is one of the groups III or IV, in which $R^4$ is hydrogen, methyl, benzyl or acetyl, $R^5$ is hydrogen or $C_1$–$C_4$-alkyl, $R_a$, $R_b$, $R_c$ and $R_d$ are methyl and $R_e$ and $R_f$ are hydrogen, and also those compounds of the formulae I and II in which $R^1$ denotes —CN, —$COCH_3$ or —$COOR^{15}$ and $R^{14}$ and $R^{15}$ are methyl or ethyl, $R^2$ is alkyl with 1–18 C atoms, cyanoethyl, benzyl or a $C_1$–$C_4$-alkyl which is substituted by one or two of the groups —COZ or —$COOR^{15}$, and, when n is 1, $R^{II}$ denotes cyanoethyl or a $C_1$–$C_4$-alkyl which is substituted by 1 or 2 of the groups —COZ, —P(O)($OR^{14}$)$_2$ or —$COOR^{15}$ and, when n is 2, $R^{II}$ can also denote $C_1$–$C_{18}$-alkyl or benzyl, and, if n is 1, $R^3$ denotes alkyl with 1–18 C atoms, allyl, benzyl, —COZ, cyanoethyl or a $C_1$–$C_4$-alkyl radical which is substituted by —COZ, —P(O)($OR^{14}$)$_2$ or —$COOR^{15}$ and, if n is 2, $R^3$ denotes alkylene with 4–10 C atoms, butenylene or arylene-bis-alkylene with 8–14 C atoms, are particularly preferred.

Also particularly preferred are compounds of the formulae I or II in which n is 1 or 2, Z is a group of the formula III or IV, in which $R^4$ is hydrogen, methyl, benzyl or acetyl, $R^5$ is hydrogen, $R_a$, $R_b$, $R_c$ and $R_d$ are methyl and $R_e$ and $R_f$ are hydrogen, $R^1$ denotes —CN or —$COCH_3$, $R_2$ is benzyl and, when n is 1, $R^{II}$ denotes cyanoethyl or $C_1$–$C_4$-alkyl substituted by 1 or 2 of the groups —COZ and, when n is 2, $R^{II}$ also denotes $C_1$–$C_{12}$-alkyl or benzyl, and, if n is 1, $R^3$ denotes $C_1$–$C_{12}$-alkyl, benzyl, —COZ, cyanoethyl or $C_1$–$C_2$-alkyl substituted by —COZ and, if n is 2, $R^3$ denotes $C_4$–$C_8$-alkylene, butenylene, xylylene or dimethylenediphenyl.

The present invention also includes the salts of compounds of the formula I or II which are formed by an addition reaction with acids in amounts which are at most equivalent to the piperidine groups. Such acids can be inorganic acids, such as, for example, sulphuric acid, hydrochloric acid or phosphoric acid, organic carboxylic acids, such as formic acid, acetic acid, oxalic acid, maleic acid, benzoic acid or salicylic acid, organic sulphonic acids, such as methanesulphonic acid or p-toluenesulphonic acid, or organic phosphorus-containing acids, such as diphenylphosphoric acid, methanephosphonic acid or diphenylphosphinic acid.

Examples of compounds of the formula I are: 2,2,6,6-tetramethyl-4-piperidinyl α-butyl-acetoacetate, 1-hexyl-2,2,6,6-tetramethyl-4-piperidinyl α,α-bis-octadecyl-acetoacetate, 1,2,2,6,6-pentamethyl-4-piperidinyl α-(2,2,6,6-tetramethyl-4-piperidinyl)-α-[1,2-bis-(1,2,2,6,6-pentamethyl-4-piperidinyloxycarbonyl)-ethyl]-cyanoacetate, 2,2,6,6-tetramethyl-4-piperidinyl 2-butenylene-1,4-bis-[α-(2,2,6,6-tetramethylpiperidinyloxycarbonylmethyl)-acetoacetate], 1,2,2,6,6-pentamethyl-4-piperidinyl p-xylylene-bis-[α-(ethoxycarbonylmethyl)-cyanoacetate], 2-(4-acetoxy-2,2,6,6-tetramethyl-1-piperidinyl)-ethyl 1-cyano-2-phenylpropionate, 1-octyl-2,2,6,6-tetramethyl-4-piperidinyl α,α-dibenzyl-acetoacetate, 1,2,2,6,6-pentamethyl-4-piperidinyl α-benzylsulphonyl-α-benzyl-isovalerate, di-(1,2,2,6,6-pentamethyl-4-piperidinyl) diethylphosphono-malonate, 1,2,2,6,6-pentamethyl-4-piperidinyl 1,4-phenylene-bis-[α-cyano-α-(1,2,2,6,6-pentamethyl-4-piperidinyl)-propionate], di-(1,2,2,6,6-pentamethyl-4-piperidinyl formylsuccinate, 1-hexyl-2,2,6,6-tetramethyl-4-piperidinyl α-benzyl-α-ethoxycarbonyl-β-phenylpropionate, N,N-di(2,2,6,6-tetramethyl-4-piperidinyl)-α-benzylacetoacetic acid amide, 1,2,2,6,6-pentamethyl-4-piperidinyl ethoxycarbonylmethyl-[β-(3,5-di-tert.-butyl-4-hydroxyphenyl)-propionyl]-acetate and bis-(1,2,2,6,6-pentamethyl-4-piperidinyl)α-(1,2,2,6,6-pentamethyl-4-piperidinyl)-α-cyano-succinate.

Examples of compounds of the formula II are: bis-(2,3,6-trimethyl-2,6-diethyl-4-piperidinyl)-butyl-[(2-ethoxycarbonyl)-ethyl]-malonate, tris-(1,2,2,6,6-pentamethyl-4-piperidinyl) tetradecane-1,2,2-tricarboxylate, tris-(1-propyl-2,2,6,6-tetramethyl-4-piperidinyl) 1-phenylethane-2,2,2-tricarboxylate, hexakis-(2,2,6,6-tetramethyl-4-piperidinyl) hexane-1,1,1,6,6,6-hexacarboxylate, tetrakis-(1,2,2,6,6-pentamethyl-4-piperidinyl)-tetradec-7-ene-5,5,10,10-tetracarboxylate, hexakis-(2,2,6,6-tetramethyl-4-piperidinyl) dodecane 1,3,3,10,10,12-hexacarboxylate, bis-(1-benzyl-2,2,6,6-tetramethyl-4-piperidinyl) bis-(β-cyanoethyl)-malonate, bis-(1,2,2,6,6-pentamethyl-4-piperidinyl) 1-phenyl-4-cyanobutane-2,2-dicarboxylate, bis-(1-acetyl-2,2,6,6-tetramethyl-4-piperidinyl) bis-(β-cyanoethyl)-malonate, tetrakis-(1,2,2,6,6-pentamethyl-4-piperidinyl) p,p'-di-(3-phenylpropyl)-diphenyl-2,2,2',2'-tetracarboxylate, bis-(1,2,2,6,6-pentamethyl-4-piperidinyl) 2-phenylpentan-4-one-1,1-dicarboxylate, tetrakis-2,2,6,6-tetramethyl-4-piperidinyl) hexadecane-5,5,12,12-tetracarboxylate, 1,10-diphenyldecane-2,2,9,9-tetracarboxylic acid tetrakis-(2,2,6,6-tetramethyl-4-piperidinyl)-amide, tetrakis-(1,2,2,6,6-pentamethyl-4-piperidinyl) 1,12-diphenyldodecane-2,2,11,11-tetracarboxylate, tetrakis-(1-benzyl-2,2,6,6-tetramethyl-4-piperidinyl) p-di-(3-phenylpropyl)-benzene-2,2,2',2'-tetracarboxylate, hexakis-(1-benzyl-2,2,6,6-tetramethyl-4-piperidinyl) p-diethyl-benzene-2,2,2',2',2'-hexacarboxylate, tris-(1,2,2,6,6-pentamethyl-4-piperidinyl)-4-phenylbutane-1,3,3,-tricarboxylate, tetrakis-(1-benzyl-2,2,6,6-tetramethyl-4-piperidinyl) 4-phenylbutane-1,2,3,3-tetracarboxylate, octakis-(1-benzyl-2,2,6,6-tetramethyl-4-piperidinyl) p-dibutylbenzene-2,2,3,4,2',2',3',4'-octacarboxylate and bis-(1,2,2,6,6-pentamethyl-4-piperidinyl) benzyl-[2-(methoxycarbonyl)-ethyl]-malonate.

The compounds of the formula I and II can be manufactured by various multi-stage processes, the individual process steps representing reactions which are in themselves known.

Compounds of the formula $R^1$—$CH_2$—COZ are preferably used as the starting materials for the manufacture of the compounds of the formula I. Depending on the meaning of $R^1$, these starting compounds are polyalkylpiperidinyl-esters or polyalkylpiperidinyl-amides of cyanoacetic acid, β-ketocarboxylic acids, sulphonoacetic acids, phosphonoacetic acids, malonic ester-acids or malonamic acids. Either first the substituent $R^2$ and then the substituent $R^3$ are introduced into these starting materials (route a) or first the substituent $R^3$ and then $R^2$ are introduced into these starting materials (route b). If $R^2$ and $R^3$ are identical, the two substituents can be introduced in one step.

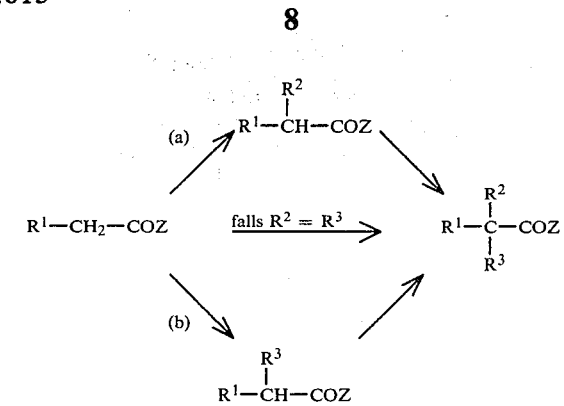

In the same way, the compounds of the formula II can be obtained from the malonates (or malonamides) of the formula $CH_2(COZ)_2$ by introducing the substituents $R^{II}$ and $R^3$ successively or at the same time.

The starting materials $R^1$—$CH_2$—COZ and $CH_2(COZ)_2$ can be manufactured by reacting the corresponding lower alkyl esters $R^1$—$CH_2$—COO—alkyl and $CH_2(COO-alkyl)_2$ respectively with the piperidine derivatives of the formula ZH. Examples of the latter compounds are 2,2,6,6-tetramethyl-4-hydroxypiperidine, 1,2,2,6,6-pentamethyl-4-hydroxypiperidine, 2,3,6-trimethyl-2,6-diethyl-4-hydroxypiperidine, 1,2,2,6,6-pentamethyl-4-methylaminopiperidine, 1-hydroxyethyl-2,2,6,6-tetramethyl-4-hydroxypiperidine or 1-(2-hydroxypropyl)-2,3,6-trimethyl-2,6-diethyl-4-acetoxypiperidine. It is also possible to react the corresponding acid chlorides $R^1$—$CH_2COCl$ and $CH_2(COCl)_2$, instead of the lower alkyl esters, with the piperidine derivatives. If $R^1$ is $CH_3CO$—, the compounds $R^1$—$CH_2$—COZ can also be manufactured by reacting ZH with diketene.

The substituents $R^2$, $R^{II}$ and $R^3$ can be introduced by adding on activated unsaturated compounds by the method of the so-called Michael addition, for example by adding on acrylonitrile, acrylates, methacrylates, acrylamides, fumaric acid derivatives or maleic acid derivatives, cinnamic acid derivatives, α-benzylideneketones, vinyl ketones, vinylphosphonates, itaconates and the like. Addition reactions of this type are usually carried out in inert solvents, such as, for example, benzene, toluene, dioxane or tetrahydrofuran, in the presence of alkaline catalysts, such as, for example, alkali metal alkoxides, alkali metal amides or quaternary ammonium hydroxides. This method is important in those cases where $R^2$, $R^{II}$ or $R^3$ is a monosubstituted or polysubstituted alkyl radical.

Another method for introducing the substituents $R^2$, $R^{II}$ and $R^3$ is the reaction with a halogen compound in the presence of molar amounts of a strong anhydrous base. Examples of such halogen compounds are benzyl chloride, butyl bromide, octyl bromide, allyl chloride, 1,6-dibromohexane, 1,8-dibromooctane, 1,10-dibromodecane, propargyl chloride, cyclohexyl bromide, cyclohexylmethyl bromide, 2,2'-dichlorodiethyl ether, 1,4-dibromobut-2-ene, 1,4-dichlorobut-2-ine, ethyl chloroacetate, ethylene glycol bis-(chloroacetate), xylylene dichloride or 4,4'-bis-(chloromethyl)-diphenyl. Examples of bases which can be used are alkali metal alkoxides, alkali metal amides, alkali metal hydrides or alkali metals. This reaction also is preferably carried out in anhydrous solvents.

If $R^2$ is a 4-piperidinyl group of the formula VI, this can be introduced by subjecting a compound $R^1$—CH$_2$—COZ to a condensation reaction with the corresponding 4-piperidone and subjecting the resulting piperidinylene compound to catalytic hydrogenation.

If $R^3$ is a group of the formula VII, such compounds are obtainable by a condensation reaction of one mol of formaldehyde with two different malonic acid derivatives or with a malonate and a compound $R^1$—CH$_2$—COZ.

If $R^3$ is a group of the formula —OR$^{21}$ or —O—C(O)R$^{22}$, this can be introduced by etherifying or esterifying the corresponding hydroxy compound (for example tartronic acid derivatives). As —OR$^{21}$, R$^3$ can also be introduced by reacting the corresponding halogen compounds (for example α-bromoacetates) with an alkali metal alkoxide.

If $R^3$ is a group of the formula —NH—C(O)R$^{22}$, this can be introduced by acylating the corresponding NH$_2$ compound, for example by means of carboxylic acid anhydrides or carboxylic acid chlorides.

The procedure for carrying out such substitution reactions for introducing $R^2$, $R^{II}$ and $R^3$ are described in even more detail in the examples which follow later in the text.

Whilst the synthesis of compounds of the formula I and II is generally begun with starting compounds which already carry the group Z only at the end of the synthesis by first introducing the substituents $R^2$, $R^{II}$ and $R^3$ into the corresponding lower alkyl esters $R^1$—CH$_2$—COO—alkyl or CH$_2$(COO—alkyl)$_2$ and then reacting the resulting substituted alkyl esters with compounds of the formula ZH. If the substituted alkyl esters are esters of polycarboxylic acids, it is possible to react all of the ester groups or only some of the ester groups with a compound ZH and this is regulated by the amount of ZH which is used. Likewise, the substituent $R^4$—when this is not hydrogen—can be introduced into the starting compounds or into intermediate products or end products obtained from the stepwise introduction of $R^2$, $R^{II}$ and $R^3$.

It should furthermore be mentioned that substituents introduced as $R^2$, $R^{II}$ or $R^3$ can be converted in a subsequent reaction. For example, the group —CH$_2$CH$_2$COOC$_2$H$_5$ can be introduced as $R^3$ by adding on ethyl acrylate and this group can then be converted into the divalent group —CH$_2$CH$_2$—COOCH$_2$CH$_2$OOC—CH$_2$CH$_2$— by transesterification with ethylene glycol. Alternatively, it is possible, starting from an alkenyl group, to obtain an alkyl group by adding on hydrogen or to obtain a phosphonoalkyl group by adding on a dialkyl phosphite.

According to the present invention, the compounds of the formula I and II can be used as stabilisers for plastics in order to protect them against damage due to the action of oxygen, heat and light. Examples of such plastics are the polymers listed on pages 12–14 of German Offenlegungsschrift No. 2,456,864.

The stabilisation of polyolefines, styrene polymers and polyamides and of polyurethanes is particularly important and the compounds of the formulae I and II are outstandingly suitable for this. Examples of such polymers are high-density polyethylene and low-density polyethylene, polypropylene, ethylene/propylene copolymers, polystyrene, styrene/butadiene/acrylonitrile copolymers, mixtures of polyolefines or of styrene polymers, and polyurethanes based on polyethers or polyesters, in the form of films, fibres, lacquers, elastomers or foams.

The stabilisers are added to the plastics in a concentration of 0.01 to 5% by weight, calculated relative to the material to be stabilised. Preferably, 0.03 to 1.5, and particularly preferentially 0.2 to 0.6, % by weight of the compounds, calculated relative to the material to be stabilised, are incorporated into the latter.

Incorporation can be effected after polymerisation, for example by mixing the compounds, and optionally further additives, into the melt by the methods customary in the art, before or during shaping, or also by applying the dissolved or dispersed compounds to the polymer, with subsequent evaporation of the solvent if necessary.

The new compounds can also be added to the plastics to be stabilised in the form of a master batch which contains these compounds, for example in a concentration of 2.5 to 25% by weight.

In the case of crosslinked polyethylene, the compounds are added prior to crosslinking.

In addition to the compounds of the formula I or II, yet further known stabilisers and costabilisers can also be added to the plastics. These stabilisers can be, for example, antioxidants, light stabilisers or metal deactivators, or also costabilisers, such as those of the phosphorous acid ester type. Furthermore, other additives customary in plastics technology, such as, for example, flameproofing agents, antistatic agents, plasticisers, lubricants, blowing agents, pigments, reinforcing materials or fillers, can also be added. Examples of individual additives which can be used together with the compounds of the formula I or II are given on pages 18–24 of German Offenlegungsschrift No. 2,427,853.

Known and customary additives of this type are not only compatible with the stabilisers of the formula I or II, but in some cases can also result in a synergistic increase in the effect.

The invention therefore also relates to plastics which are stabilised by the addition of 0.01 to 5% by weight of a compound of the formula I or II and which optionally can also contain other known and customary additives. The plastics stabilised in this way can be used in very diverse forms, for example as films, fibres, tapes or profiles or as binders for lacquers, adhesives or putties.

The manufacture and use of the compounds according to the invention is described in more detail in the examples which follow. In these examples, parts denote parts by weight and % denote percentages by weight. The temperatures are given in degrees Centigrade.

EXAMPLE 1

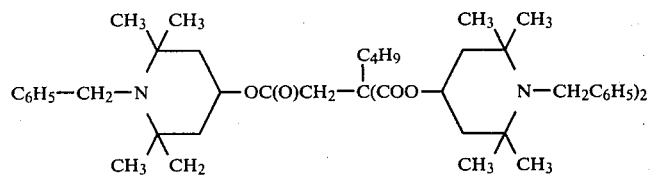

30.2 g (0.1 mol) of triethyl hexane-1,2,2-tricarboxylate, 74.2 g (0.3 mol) of 1-benzyl-2,2,6,6-tetramethyl-4-hydroxypiperidine and 50 ml of xylene are warmed to 130° and mixed with 0.8 g of LiNH$_2$. The ethanol formed is distilled off continuously. The solution is kept at the above temperature for 3 hours, so that it can then be kept at 150° for a further 2 hours. After cooling, the residue is taken up in toluene, a little glacial acetic acid is added to the solution and the latter is washed with H$_2$O. After drying over Na$_2$SO$_4$, the solvent is distilled off in vacuo. Tris-(1-benzyl-2,2,6,6-tetramethyl-4-piperidinyl)hexane-1,2,2-tricarboxylate is obtained as a powdery residue. (Compound No. 1).

Calculated: N=4.66%, Found: N=4.2%.

EXAMPLES 2–5

The compounds which follow are manufactured analogously to Example 1 by reacting the corresponding ethyl ester with 4-hydroxypiperidines.

can be kept at 35°–40° C. by means of slight external cooling. The mixture is then stirred at room temperature for a further 14 hours. For working up, the reaction mixture is washed three times with water and dried over sodium sulphate and the solvent is distilled off in vacuo. The residue, which solidifies as a crystalline product, melts at 61°–62° C. after recrystallisation from acetonitrile. The product is bis-(2,2,6,6-tetramethyl-4-piperidinyl) bis-β-cyanoethyl)-malonate.

Compounds No. 7–9 are manufactured analogously by an addition reaction of acrylonitrile with the corresponding malonates.

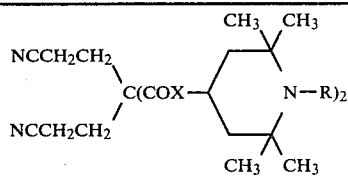

| Compound No. | Formula | Melting point |
|---|---|---|
| 2 | (HN⟨piperidinyl⟩—OC(O)CH$_2$)$_2$C(COO—⟨piperidinyl⟩NH)$_2$ | 207–209° |
| 3 | (CH$_3$—N⟨piperidinyl⟩—OC(O)CH$_2$)$_2$C(COO—⟨piperidinyl⟩N—CH$_3$)$_2$ | 145° |
| 4 | CH(COO—⟨piperidinyl N—CH$_3$⟩)$_3$ | 72–75° |
| 5 | ( CH ⟨COO—piperidinyl N—CH$_2$—C$_6$H$_5$⟩ )$_3$ | amorphous<br>N calculated 4.3%<br>found 4.4% |

EXAMPLES 6–9

57.3 g of bis-(2,2,6,6-tetramethyl-4-piperidinyl) malonate are dissolved in 150 ml of anhydrous benzene. 0.5 ml of a freshly prepared 10% strength solution of sodium ethoxide in ethanol is added to this solution. 16.4 g of freshly distilled acrylonitrile are then added dropwise, whilst stirring, at such a rate that the temperature

| Compound No. | X | R | Melting point |
|---|---|---|---|
| 6 | —O— | H | 61–62° |

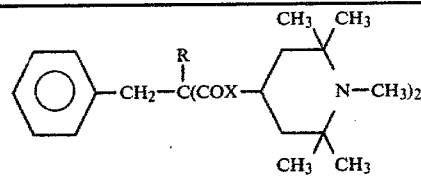

| Compound No. | R | X | Melting point |
|---|---|---|---|
| 11 | NC—CH₂CH₂— | O | 90–91° |
| 12 | NC—CH₂CH₂— | NH | 195–197° |
| 13 | CH₂CH₂—) | O | amorphous N calculated 6.1% found 6.0% |

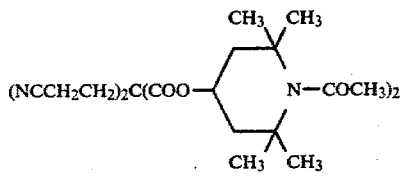

| Compound No. | X | R | Melting point |
|---|---|---|---|
| 7 | —O— | —CH₂—phenyl | 190–191° |
| 8 | —O— | CH₃ | 126–127° |
| 9 | —NH— | CH₃ | 246–249° |

EXAMPLE 10

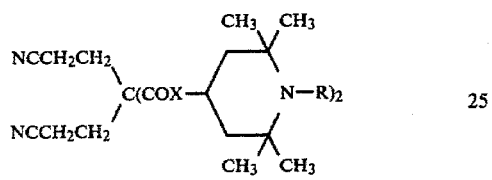

24.5 g of bis-(2,2,6,6-tetramethyl-4-piperidinyl) bis-(β-cyanoethyl)-malonate (compound No. 4) are suspended in 80 ml of acetic anhydride and the suspension is heated to 80°–85° C. for 36 hours, whilst stirring. For working up, the excess acetic anhydride is distilled off as completely as possible in vacuo and the residue is taken up in methylene chloride and the solution is washed three times with 10% strength sodium carbonate solution and then three times with water. The methylene chloride phase, which is now neutral, is dried over sodium sulphate, the solvent is distilled off and the crude compound is recrystallised from isopropanol and, by this means, pure bis-(1-acetyl-2,2,6,6-tetramethyl-4-piperidinyl) bis-(β-cyanoethyl)-malonate with a melting point of 103°–104° is obtained (compound No. 10).

EXAMPLE 11–13

Bis-(2,2,6,6-tetramethyl-4-piperidinyl) benzylmalonate and benzylmalonic acid bis-(2,2,6,6-tetramethyl-4-piperidinyl)-amide are reacted in the manner described in Example 6 with 1 mol of acrylonitrile or with 1 mol of 1,2,2,6,6-pentamethyl-4-piperidinyl acrylate, the following compounds being obtained:

EXAMPLE 14

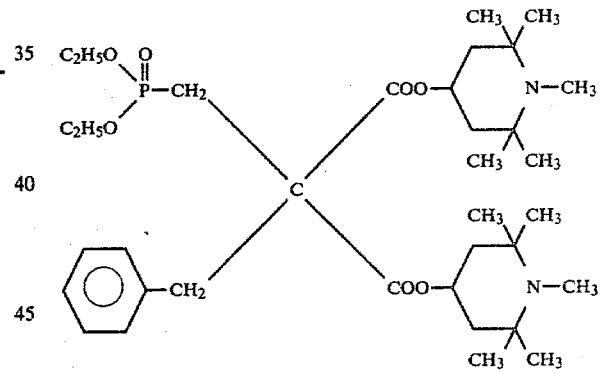

A solution of 0.92 g of sodium in 50 ml of ethanol is added dropwise at room temperature to a mixture of 22.4 g (0.04 mol) of bis-(1,2,2,6,6-pentamethyl-4-piperidinyl) diethylphosphonomethylmalonate and 6.8 g (0.04 ml) of benzyl bromide in 50 ml of ethanol. After stirring for 2 hours at room temperature and 20 hours under reflux, the solvent is distilled off and replaced by toluene. This solution is washed with water and dried over Na₂SO₄. The solvent is then stripped off under reduced pressure and 25.1 g of bis-(1,2,2,6,6-pentamethyl-4-piperidinyl) benzyl-(diethylphosphonomethyl)-malonate are obtained in the form of a viscous oil (compound No. 14).

Analysis: calculated: N: 4.31%, P: 4.76%; found: N: 4.4%, P: 4.5%.

Bis-(1,2,2,6,6-pentamethyl-4-piperidinyl) diethylphosphonomethylmalonate which is used as the starting material can be prepared by reacting bis-(1,2,2,6,6-pentamethyl-4-piperidinyl) malonate with 1 mol of paraformaldehyde and 1 mol of triethyl phosphite.

EXAMPLE 15

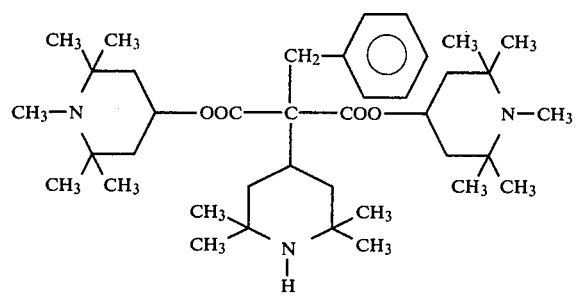

2.1 g (0.05 mol) of a 55–60% strength dispersion of NaH in oil are added to a solution of 27.4 g of bis-(1,2,2,6,6-pentamethyl-4-piperidinyl) (2,2,6,6-tetramethyl-4-piperidinyl)-malonate in 150 ml of toluene. After stirring for 5 hours at 100° C., 8.5 g (0.05 mol) of benzyl bromide in 50 ml of toluene are added dropwise at −30° C. The mixture is refluxed for 15 hours, cooled to room temperature and washed with water and the toluene solution is dried over $Na_2SO_4$. The solvent is then distilled off under reduced pressure and after one recrystallisation of the residue from acetonitrile 24 g of bis-(1,2,2,6,6-pentamethyl-4-piperidinyl) benzyl-(2,2,6,6-tetramethyl-4-piperidinyl)-malonate which melts at 102°–103° C. are obtained (compound No. 15).

Analysis: calculated: N: 6.53%; found: N: 6.3%.

EXAMPLE 16

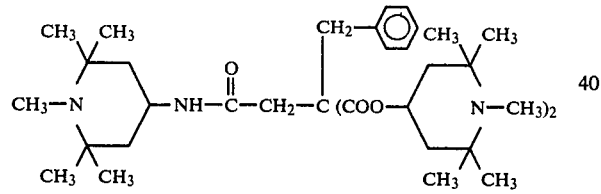

Compound No. 16 of the above formula, which melts at 150°–152°, is prepared analogously to Example 14 by reacting bis-(1,2,2,6,6-pentamethyl-4-piperidinyl) benzylmalonate with N-(1,2,2,6,6-pentamethyl-4-piperidinyl)-chloroacetamide.

EXAMPLE 17

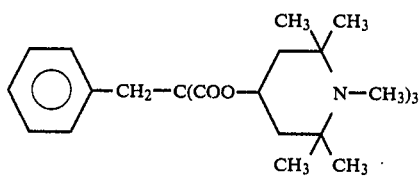

Compound No. 17 of the above formula is prepared by benzylation of tris-(1,2,2,6,6-pentamethyl-4-piperidinyl) methanetricarboxylate by the method described in Example 12 and is obtained in the form of an amorphous resin.

Analysis: calculated: N 6.01%; found: N 5.70%.

EXAMPLE 18

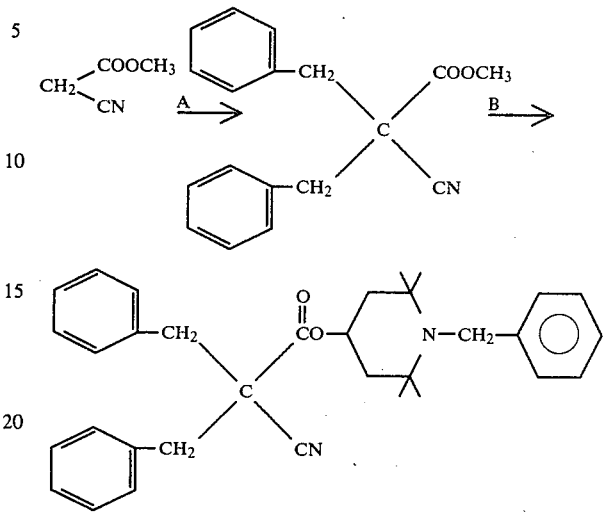

(A) A solution of 83.1 g (1.54 mols) of sodium methoxide in 450 ml of absolute methanol is added dropwise in the course of about 4 hours to a solution, which has been warmed to about 80° C., of 60.9 g (0.7 mol) of methyl cyanoacetate and 263.3 g (1.54 mols) of benzyl bromide in 350 ml of ligroin (boiling point 110°–140°), whilst stirring vigorously. During the addition, the methanol is continuously distilled off, and separated off, with the aid of a water separator at approximately the same rate as it is added dropwise, in the form of the sodium methoxide solution, to the reaction mixture. After the sodium methoxide solution has been added, the mixture is heated for 1 hour longer, whilst methanol is still separated off. The internal temperature has risen to about 90° C. in the meantime. For working up, the reaction mixture is cooled to room temperature, 300 ml of diethyl ether are added and the resulting mixture is extracted repeatedly with water. The organic phase is separated off and dried over sodium sulphate, the solvent is distilled off in vacuo in a rotary evaporator and the residue, which solidifies as a substantially crystalline product, is recrystallised once from a little diethyl ether and then from diethyl ether/n-hexane and by this means pure methyl dibenzyl-cyanoacetate with a melting point of 80°–81° is obtained.

(B) 0.1 g of lithium amide is added to a solution, which has been heated to about 120° C., of 22.4 g of methyl dibenzylcyanoacetate and 19.8 g of 1-benzyl-2,2,6,6-tetramethyl-4-hydroxy-piperidine in 250 ml of anhydrous zylene, whilst stirring. The reaction mixture is heated up to about 137° in the course of 4 hours whilst, at the same time, passing a gentle stream of nitrogen through the mixture and the methanol liberated, and also some of the xylene, is distilled off slowly through a descending condenser. The internal temperature is then raised to 147°–150° and the remaining xylene is distilled off slowly (over a period of about 4 hours). After cooling to room temperature, the reaction mixture is dissolved in 200 ml of methylene chloride, the solution is washed repeatedly with water and dried over sodium sulphate, the solvent is distilled off and the residue, which after some time solidifies as a crystalline product, is recrystallised from n-hexane and by this means pure 1-benzyl-2,2,6,6-tetramethyl-4-piperidinyl dibenzylcyanoacetate with a melting point of 111°–112° is obtained. (Compound No. 18).

EXAMPLE 19

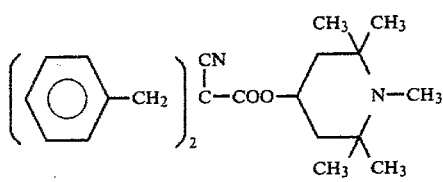

1,2,2,6,6-Pentamethyl-4-piperidinyl dibenzyl-cyanoacetate, which melts at 78°–79°, is prepared analogously to Example 18 (compound No. 19).

EXAMPLES 20–22

0.8 ml of a 10% strength solution of sodium ethoxide in ethanol is added, at 30° C., to a solution of 15.4 g of bis(1,2,2,6,6-pentamethyl-4-piperidinyl) malonate and 12 g of diethyl vinylphosphonate in 15 ml of dioxane, whilst stirring, and the mixture is stirred at 33°–36° C. for 24 hours. The dioxane is then distilled off in vacuo, water is added to the residue and the resulting mixture is extracted repeatedly with diethyl ether. The combined ether extracts are washed twice with 100 ml of 0.1 N acetic acid and twice with water and dried over sodium sulphate, and the solvent and any excess diethyl vinylphosphonate which may still be present are removed in vacuo or under a high vacuum at a maximum of 70° C. The crude product, which after some time solidifies as a crystalline product, is recrystallised from n-hexane and by this means pure bis-(1,2,2,6,6-pentamethyl-4-piperidinyl) bis-(2-diethylphosphono-ethyl)-malonate with a melting point of 81°–82° C. is obtained. (Compound No. 20). Compound No. 21 is prepared analogously. Compound No. 22 is prepared by acetylation of compound No. 21 by the method described in Example 10.

[(C₂H₅O)₂(O)P—CH₂CH₂]₂—C(COO—⟨piperidinyl with N—R⟩)₂

| Compound No. | R | Melting point |
|---|---|---|
| 20 | CH₃ | 81–82° |
| 21 | H | 86–87° |
| 22 | —COCH₃ | 77–79° |

EXAMPLE 23

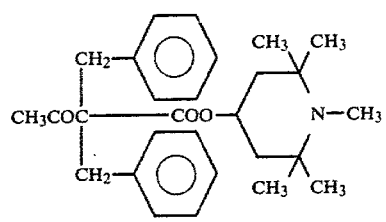

A solution of 48.6 g (0.2 mol) of 1,2,2,6,6-pentamethyl-4-piperidinyl acetoacetate in 300 ml of toluene is added dropwise at room temperature to a mixture of 16.7 g (0.4 mol) of a 55–60% dispersion of NaH in mineral oil and 200 ml of toluene. After stirring for 4 hours under reflux, the reaction mixture is cooled to −30° and 68.5 g (0.4 mol) of benzyl bromide in 40 ml of toluene are added dropwise. The mixture is then heated under reflux for 15 hours and after cooling to room temperature is washed with water. The toluene solution is dried over Na₂SO₄ and the solvent is distilled off under reduced pressure. This gives 68.6 g of 1,2,2,6,6-pentamethyl-4-piperidinyl 2,2-dibenzyl-acetoacetate in the form of a viscous yellowish oil (compound No. 23).
Analysis: calculated: N 3.22%; found: N 3.1%.

EXAMPLES 24 and 25

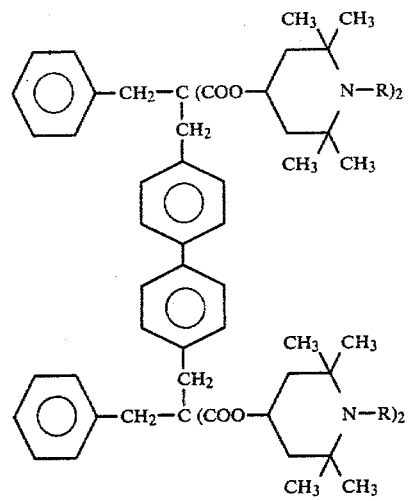

Compound 24; R=—CH₃
Compound 25: R=

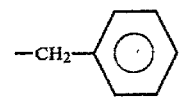

3.84 g of sodium hydride (50% strength suspension in mineral oil) are washed twice with hexane (removal of the mineral oil) under N₂ in a 4-necked flask and are then covered with a layer of 20 ml of dimethylformamide (DMF). A solution of 40 g of bis-(1,2,2,6,6-pentamethyl-4-piperidinyl) benzylmalonate in 60 ml of dimethylformamide is added dropwise to this suspension in the course of about 1 hour, at room temperature and whilst stirring. In order to complete the removal of the proton, the mixture is heated to 80° for a further 3 hours. After cooling the reaction mixture, a solution of 10 g of p,p'-bis-chloromethyl-diphenyl in 50 ml of DMF is then added dropwise in the course of about 30 minutes at room temperature, whilst stirring, and the mixture is then stirred for a further 14 hours at 75°. For working up, water is added to the cooled reaction mixture and the resulting mixture is repeatedly extracted with an ether/hexane mixture (1:1). The combined organic phases are washed with water and saturated sodium chloride solution and dried over sodium sulphate, the solvent is distilled off and the residue is twice recrystallised from ligroin (boiling point 110°–140°) and, by this means, pure tetra-(1,2,2,6,6-pentamethyl-4-piperidinyl) p,p'-di-(3-phenylpropyl)-diphenyl-2,2,2',2'-tetracarboxylate with a melting point of 174°–175° C. is obtained (compound No. 24).

Bis-(1,2,2,6,6-pentamethyl-4-piperidinyl) benzylmalonate (melting point: 69°–70°) which serves as an intermediate product, was prepared by catalytic hydrogenation (palladium-on-charcoal: in dioxane) from bis-(1,2,2,6,6-pentamethyl-4-piperidinyl) benzylidene-malonate.

The bis-(1,2,2,6,6-pentamethyl-4-piperidinyl) benzylidene-malonate (melting point: 116°–117°), which, in turn, again serves as an intermediate product, was prepared by a condensation reaction of bis-(1,2,2,6,6-pentamethyl-4-piperidinyl) malonate with benzaldehyde (azeotropic distillation in benzene with the addition of 0.04 mol of glacial acetic acid and 0.04 mol of piperidine per mol of the components).

Compound No. 25 of the above formula, which melts at 172°–175°, was obtained analogously.

EXAMPLES 26-32

A solution of 23.6 g of bis-(2,2,6,6-tetramethyl-4-piperidinyl) benzylmalonate in 100 ml of toluene and 20 ml of dimethylformamide is added dropwise, at 40°, in the course of about 30 minutes to a suspension of 1.2 g of oil-free sodium hydride in 20 ml of toluene, whilst stirring. After stirring for a further 5 hours at 80°, all of the sodium hydride has reacted. A solution of 6.7 g of dibromohexane in 20 ml of toluene is then added dropwise to the reaction mixture and the resulting mixture is stirred for a further 16 hours at 80°. After cooling to room temperature, the sodium bromide which has precipitated is filtered off from the reaction solution, the filtrate is washed repeatedly with water, the organic phase is dried over sodium sulphate and all of the solvent is distilled off in vacuo. Repeated recrystallisation from acetonitrile gives pure tetrakis-(2,2,6,6-tetramethyl-4-piperidinyl) 1,10-diphenyldecane-2,2,9,9-tetracarboxylate with a melting point of 129°–130° (compound No. 26).

Compounds No. 27–31 were prepared analogously. Compound No. 32 was obtained by catalytic hydrogenation of compound No. 31.

$$(R_1-N\underset{CH_3\ CH_3}{\overset{CH_3\ CH_3}{\diagdown\diagup}}X-CO)_2\ \underset{R_2}{\overset{R_2}{C-R_3-C}}(CO-X-\underset{CH_3\ CH_3}{\overset{CH_3\ CH_3}{\diagup\diagdown}}N-R_1)_2$$

| Compound No. | X | $R_1$ | $R_2$ | $R_3$ | Melting point |
|---|---|---|---|---|---|
| 26 | O | H | Benzyl | $(CH_2)_6$ | 129–130° |
| 27 | O | H | Butyl | $(CH_2)_6$ | 92–94° |
| 28 | O | $CH_3$ | Benzyl | $(CH_2)_8$ | 154–156° |
| 29 | NH | H | Benyzl | $(CH_2)_6$ | 252–254° |
| 30 | NH | $CH_3$ | Benzyl | $(CH_2)_{10}$ | 243–245° |
| 31 | O | $CH_3$ | Benzyl | $CH_2CH=CHCH_2$ | 197–199° |
| 32 | O | $CH_3$ | Benzyl | $(CH_2)_4$ | 193–194° |

EXAMPLE 33

100 parts of polypropylene powder (Moplen, fibre grade, from Messrs. Montedison) are homogenised with 0.2 part of octadecyl $\beta$-(3,5-di-tert.-butyl-4-hydroxyphenyl)-propionate and 0.25 part of a stabiliser from Table I which follows for 10 minutes in a Brabender plastograph at 200° C. The composition which is thus obtained is removed from the kneader as rapidly as possible and pressed in a toggle press to give a 2–3 mm thick sheet. Part of the resulting pressed blank is cut out and pressed between two high-gloss hard aluminium foils for 6 minutes at 260° and under a pressure of 40 kg/cm², using a laboratory press, to give a 0.1 mm thick film, which is immediately plunged into cold water. Cut pieces, each measuring 60×44 mm are now punched from this film and exposed in a Xenotest 150. These test pieces are removed from the exposure apparatus at regular intervals and their carbonyl content is tested in an IR spectrophotometer. The increase in the carbonyl extinction at 5.85$\mu$ on exposure is a measure of the photo-oxidative degradation of the polymer (see L. Balaban et al., H. Polymer Sci. Part C, 22, 1059–1071 (1969)) and, according to experience, is associated with a deterioration of the mechanical properties of the polymer. Thus, for example, the film is completely brittle when a carbonyl extinction of about 0.300 is reached.

The protective action of the stabilisers according to the invention can be seen from Table I which follows:

TABLE I

| Light stabiliser Compound No. | Xenotest 150 Exposure time in hours until the extinction is 0.3 at 5.85$\mu$ |
|---|---|
| None | 1,100 |
| 2 | 9,100 |
| 3 | >7,200 |
| 8 | 6,000 |
| 24 | 4,300 |
| 26 | 6,200 |
| 28 | 5,800 |
| 29 | 6,000 |

EXAMPLE 34

0.1 mm thick polypropylene films are produced as described in Example 33. However, these are exposed to more intense radiation in a Xenotest 1,200. The light stabilisers used are listed in Table II.

TABLE II

| Light stabiliser Compound No. | Xenotest 1,200 Exposure time in hours until the extinction is 0.3 at 5.85μ |
|---|---|
| None | 550 |
| 1 | >3,600 |
| 5 | >1,360 |
| 6 | >3,700 |
| 7 | >3,600 |
| 9 | > 900 |
| 10 | >2,000 |
| 11 | >4,000 |
| 12 | > 900 |
| 13 | > 900 |
| 20 | >1,400 |
| 21 | > 900 |
| 22 | >1,800 |
| 25 | >3,200 |
| 27 | >6,200 |
| 30 | >1,400 |
| 32 | >3,700 |

What is claimed is:

1. A compound of the formula I or II

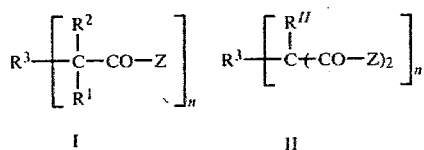

I      II and its salts, in which n is 1 or 2, Z is a group of the formula III, IV or V

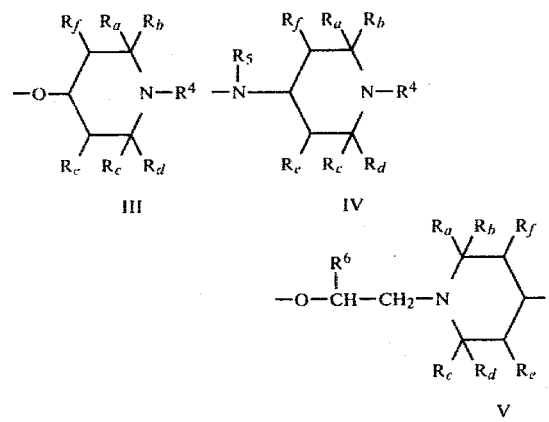

III     IV

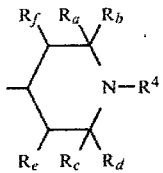

V in which $R^4$ represents hydrogen, O·, —OH, alkyl with 1–12 C atoms, alkenyl with 3 or 4 C atoms, propargyl, benzyl or a group of the formula —CH$_2$—CH(OR$^9$-)—R$^8$, in which R$^8$ denotes hydrogen, methyl or phenyl and R$^9$ denotes hydrogen or a group A—CO—; or R$^4$ denotes a group A—CO— and in both cases A denotes alkyl with 1–17 C atoms, alkenyl with 2 or 3 C atoms, cyclohexyl, phenyl, benzyl or a phenyl, phenylmethyl or phenylethyl group which is substituted by 2 alkyl groups, each with 1–4 C atoms, and a hydroxyl group, or denotes alkylamino with 1–12 C atoms, dialkylamino with 2–16 C atoms, anilino, alkoxy with 1–12 C atoms, benzyloxy or phenoxy, $R^5$ denotes hydrogen, alkyl with 1–18 C atoms, alkenyl with 3–6 C atoms, propargyl, cycloalkyl with 5–12 C atoms, aralkyl with 7–14 C atoms, which can be substituted by OH, or a group of the formula VI $R^6$ is hydrogen, methyl or phenyl, $R^7$ denotes hydrogen, —OR$^{10}$ or —N(R$^{11}$)(R$^{12}$) and R$^{10}$ denotes alkyl with 1–18 C atoms, alkenyl with 3–6 C atoms, benzyl, 2-cyanoethyl or an aliphatic, cycloaliphatic, aromatic or araliphatic acyl group which has up to 18 C atoms and can be substituted in the aromatic part by halogen, alkoxy with 1–4 C atoms, alkyl with 1–4 C atoms and/or hydroxyl, $R^{11}$ is alkyl with 1–18 C atoms, alkenyl with 3–6 C atoms or phenylalkyl with 7–9 C atoms and $R^{12}$ has the same meaning as $R^{11}$ or represents an aliphatic, cycloaliphatic, aromatic or araliphatic acyl group which has up to 18 C atoms and can be substituted in the aromatic part by halogen, alkoxy with 1–4 C atoms, alkyl with 1–4 C atoms and/or hydroxyl, $R_a$ denotes alkyl with 1–6 C atoms, $R_b$ denotes alkyl with 1–6 C atoms, $R_c$ denotes alkyl with 1–9 C atoms, phenyl, benzyl or phenylethyl and $R_d$ denotes alkyl with 1–6 C atoms, or $R_c$ and $R_d$ conjointly denote tetramethylene or pentamethylene, $R_e$ denotes hydrogen, alkyl with 1–5 C atoms, alkenyl or alkinyl with 3–4 C atoms or benzyl and $R_f$ denotes hydrogen, alkyl with 1–5 C atoms or benzyl and the positions of $R_e$ and $R_f$ can be exchanged, and $R^1$ denotes one of the groups —CN, —CHO, —COR$^{13}$, —SO$_2$R$^{13}$, —P(O)(OR$^{14}$)$_2$, —P(O)(C$_6$H$_5$)$_2$, —COOR$^{15}$ or —CON(R$^{16}$)(R$^{17}$), in which R$^{13}$ denotes alkyl with 1–18 C atoms, cyclohexyl, aryl which has 6–10 C atoms and can be substituted by chlorine or C$_1$–C$_8$-alkyl, phenylalkyl with 7–9 C atoms or a phenyl or phenylalkyl radical which is substituted by one or two C$_1$–C$_4$-alkyl groups and/or hydroxyl, R$^{14}$ denotes alkyl with 1–18 C atoms, aryl with 6–10 C atoms or aralkyl with 7–9 C atoms, R$^{15}$ denotes alkyl with 1–18 C atoms, alkenyl with 3–6 C atoms, phenyl, phenylalkyl with 7–9 C atoms or alkylphenyl with 7–14 C atoms and R$^{16}$ and R$^{17}$ independently of one another denote hydrogen, alkyl with 1–12 C atoms, cyclohexyl, benzyl or phenyl, R$^2$ denotes hydrogen, alkyl with 1–20 C atoms, alkenyl or alkinyl with 3–4 C atoms, aralkyl with 7–11 C atoms, phenyl, —COZ, —COOR$^{15}$ or an alkyl group which has 1–10 C atoms and is substituted by one or two of the groups —CN, —COZ, —P(O)(OR$^{14}$)$_2$, —COOR$^{15}$ or —CON(R$^{16}$)(R$^{17}$) on different C atoms, or denotes a group of the formula VI, and, when n is 1, R$^{II}$ denotes —COZ, —COOR$^{15}$ or an alkyl group which has 1–10 C atoms and is substituted by one or two of the groups —CN, —COZ, —P(O)(OR$^{14}$)$_2$, —COOR$^{15}$ or —CON(R$^{16}$)(R$^{17}$) on different C atoms, or denotes a group of the formula VI, and, if R$^3$ is a —COZ group, can also be hydrogen, and when n is 2, R$^{II}$ can also denote alkyl with 1–20 C atoms, alkenyl or alkinyl with 3–6 C atoms, aralkyl with 7–11 C atoms or phenyl, and, when n is 1, R$^3$ denotes alkyl with 1–20 C atoms or an alkyl group which has 1–10 C atoms and is substituted by one or more of the groups —CN, —COZ, —COOR$^{15}$, —SO$_2$R$^{13}$, —CON(R$^{16}$)(R$^{17}$), —COR$^{18}$ or —P(O)(OR$^{14}$)$_2$, in which R$^{18}$ denotes alkyl with 1–12 C atoms, or R$^3$ denotes a group of the formula

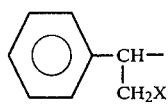

in which X represents —CN, —COR$^{19}$, —COOH, —COOR$^{20}$ or —COZ, R$^{19}$ represents alkyl with 1-5 C atoms or phenyl and R$^{20}$ represents alkyl with 1-18 C atoms, allyl, cyclohexyl or benzyl, and R$^3$ furthermore represents one of the groups —COZ or —COOR$^{15}$, an alkyl group which has 3-18 C atoms and is interrupted by —SO$_2$—, or alkenyl with 3-18 C atoms, alkinyl with 3-8 C atoms, cycloalkyl with 5-12 C atoms, alkylcycloalkyl with 6-18 C atoms, cycloalkyl-alkyl with 6-14 C atoms, aralkyl or alkyl-aralkyl with 7-19 C atoms, phenyl or a group —OR$^{21}$, in which R$^{21}$ can be alkyl with 1-18 C atoms, alkenyl with 3-4 C atoms, alkinyl with 3-4 C atoms or phenylalkyl with 7-9 C atoms, or R$^3$ represents a group —O—C(O)R$^{22}$ or —NH—C-(O)R$^{22}$, in which R$^{22}$ can be alkyl with 1-12 C atoms, alkenyl with 2 or 3 C atoms, cyclohexyl, phenyl, benzyl or a phenyl, phenylmethyl or phenylethyl group which is substituted by 2 alkyl groups, each with 1-4 C atoms, and a hydroxyl group, or R$^3$ represents a group of the formula VII

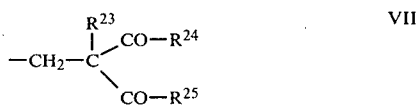

in which R$^{23}$ represents alkyl with 1-20 C atoms, allyl, benzyl, phenyl or a group —O—C(O)R$^{22}$ or —NH—C-(O)R$^{22}$, which is as defined above, and R$^{24}$ and R$^{25}$ independently of one another represent alkoxy with 1-6 C atoms or have one of the meanings indicated for Z and, when n is 2, R$^3$ represents a direct bond, alkylene with 1-20 C atoms, alkylene which has 2-10 C atoms and is interrupted by —O—, arylene-bis-alkylene with 8-14 C atoms, alkenylene with 4-8 C atoms, alkinylene with 4-8 C atoms or a group of the formula —C$_m$H$_{2m}$—COO—Y—OCO—C$_m$H$_{2m}$—, in which Y denotes alkylene with 2-12 C atoms, butenylene, butinylene, cyclohexylene or a group of the formula VIII

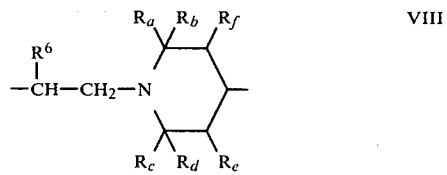

and m denotes a number from 1 to 4, but R$^1$ cannot be the group —CN when one of the substituents R$^2$, R$^{II}$ or R$^3$ has the meaning —COZ.

2. A compound according to claim 1, of the formulae I or II, in which n is 1 or 2, Z is one of the groups of the formula III, IV or V, in which R$^4$ denotes hydrogen, O·, C$_1$–C$_6$-alkyl, allyl, propargyl, benzyl, formyl, acetyl, acryloyl or crotonoyl, R$^5$ denotes hydrogen, C$_1$–C$_{12}$-alkyl, cyclohexyl, benzyl or phenyl, R$^6$ denotes hydrogen, R$^7$ denotes hydrogen or —OR$^{10}$ and R$^{10}$ denotes hydrogen, C$_1$–C$_6$-alkyl, alkanoyl with 2-12 C atoms, benzoyl or benzyl, R$_a$, R$_b$, R$_c$ and R$_d$ are methyl and R$_e$ and R$_f$ are hydrogen, or R$_a$ and R$_c$ are ethyl, R$_b$, R$_d$ and R$_e$ are methyl and R$_f$ is hydrogen, and R$^1$, R$^2$, R$^{II}$ and R$^3$ have the meaning indicated in claim 1.

3. A compound according to claim 1, of the formulae I or II, in which n is 1 or 2, Z has the meaning indicated in claim 2, R$^1$ denotes —CN, —CHO, —COR$^{13}$, —P-(O)(OR$^{14}$)$_2$ or —COOR$^{15}$, in which R$^{13}$ is C$_1$–C$_4$-alkyl or phenyl, R$^{14}$ is C$_1$–C$_4$-alkyl and R$^{15}$ is C$_1$–C$_{12}$-alkyl, R$^2$ denotes hydrogen, C$_1$–C$_{20}$-alkyl, allyl, propargyl, benzyl, —COZ, —COOR$^{15}$, a group of the formula VI or a C$_1$–C$_4$-alkyl which is substituted by one or two of the groups —CN, —COZ, —COOR$^{15}$ or —CON(R$^{16}$)(R$^{17}$) on different C atoms, and R$^{16}$ and R$^{17}$ independently of one another are hydrogen, C$_1$–C$_{12}$-alkyl, cyclohexyl or benzyl and, when n is 1, R$^{II}$ denotes —COZ, —COOR$^{15}$, a group of the formula VI or a C$_1$–C$_4$-alkyl which is substituted by 1 or 2 of the groups —CN, —COZ, —P(O)(OR$^{14}$)$_2$, —COOR$^{15}$ or —CON(R$^{16}$)(R$^{17}$) on different C atoms and, when n is 2, R$^{II}$ can also denote C$_1$–C$_{20}$-alkyl, allyl, propargyl or benzyl, and, if n is 1, R$^3$ denotes C$_1$–C$_{12}$-alkyl, a C$_1$–C$_4$-alkyl which is substituted by one of the groups —CN, —COR$^{13}$ or —P(O)(OR$^{14}$)$_2$ or by one or two of the groups —COZ, —COOR$^{15}$ or —CON(R$^{16}$)(R$^{17}$), or denotes a group of the formula VII, in which R$^{21}$ is C$_1$–C$_{12}$-alkyl or benzyl and R$^{22}$ and R$^{23}$ represent C$_1$–C$_6$-alkoxy or have the meaning indicated for Z, or, if n is 2, R$^3$ represents C$_1$–C$_{12}$-alkylene, C$_8$–C$_{14}$-arylene-bis-alkylene, butenylene, butinylene or a group of the formula —C$_m$H$_{2m}$—COO—Y-OCO—C$_m$H$_{2m}$—, in which Y denotes C$_2$–C$_8$-alkylene and m denotes 1 or 2.

4. A compound according to claim 1, of the formulae I or II, in which n is 1 or 2, Z is a group of the formula III or IV, in which R$^4$ is hydrogen, methyl, benzyl or acetyl, R$^5$ is hydrogen or C$_1$–C$_4$-alkyl, R$_a$, R$_b$, R$_c$ and R$_d$ are methyl and R$_e$ and R$_f$ are hydrogen and R$^1$, R$^2$, R$^{II}$ and R$^3$ have the meaning indicated in claim 3.

5. A compound according to claim 1, of the formulae I or II, in which n is 1 or 2, Z has the meaning indicated in claim 4, R$^1$ denotes —CN, —COCH$_3$ or —COOR$^{15}$ and R$^{14}$ and R$^{15}$ are methyl or ethyl, R$^2$ is C$_1$–C$_{18}$-alkyl, cyanoethyl, benzyl or a C$_1$–C$_4$-alkyl which is substituted by one or two of the groups —COZ or —COOR$^{15}$ and, when n is 1, R$^{II}$ denotes cyanoethyl or a C$_1$–C$_4$-alkyl which is substituted by 1 or 2 of the groups —COZ, —P(O)(OR$^{14}$)$_2$ or —COOR$^{15}$ and, when n is 2, R$^{II}$ can also denote C$_1$–C$_{18}$-alkyl or benzyl, and, if n is 1, R$^3$ denotes C$_1$–C$_{18}$-alkyl, allyl, benzyl, COZ, cyanoethyl or a C$_1$–C$_4$-alkyl which is substituted by —COZ, —P(O)(OR$^{14}$)$_2$ or —COOR$^{15}$ and, if n is 2, R$^3$ denotes C$_4$–C$_{10}$-alkylene, C$_8$–C$_{14}$-arylene-bis-alkylene or butenylene.

6. A compound according to claim 1, of the formulae I or II, in which n is 1 or 2, Z is a group of the formula III or IV, in which R$^4$ is hydrogen, methyl, benzyl or acetyl, R$^5$ is hydrogen, R$_a$, R$_b$, R$_c$ and R$_d$ are methyl and R$_e$ and R$_f$ are hydrogen, R$^1$ denotes —CN or —COCH$_3$, R$^2$ is benzyl and, when n is 1, R$^{II}$ denotes cyanoethyl or C$_1$–C$_4$-alkyl substituted by 1 or 2 of the groups —COZ and, when n is 2, R$^{II}$ also denotes C$_1$–C$_{12}$-alkyl or benzyl, and, if n is 1, R$^3$ denotes C$_1$–C$_{12}$-alkyl, benzyl, —COZ, cyanoethyl or C$_1$–C$_2$-alkyl substituted by —COZ and, if n is 2, R$^3$ denotes C$_4$–C$_8$-alkylene, butenylene, xylylene or dimethylenediphenyl.

7. A compound according to claim 1, of the formula II, in which n, Z, R$^{II}$ and R$^3$ have the meanings indicated in claim 5 or 6.

* * * * *